United States Patent [19]

Ober

[11] Patent Number: 4,535,779
[45] Date of Patent: Aug. 20, 1985

[54] TRANSCUTANEOUS ELECTRODE DEVICE FOR CAST-COVERED SITES

[75] Inventor: Stephen H. Ober, Chaska, Minn.

[73] Assignee: EMPI, Inc., Fridley, Minn.

[21] Appl. No.: 472,086

[22] Filed: Mar. 4, 1983

[51] Int. Cl.³ .......................... A61B 5/04; A61N 1/04
[52] U.S. Cl. .................................... 128/644; 128/802; 128/803
[58] Field of Search ............... 128/639, 640, 641, 644, 128/783, 798, 799, 802, 803, 792, 82.1, 419 F

[56] References Cited

U.S. PATENT DOCUMENTS

| | | | |
|---|---|---|---|
| 2,318,207 | 5/1943 | Ellis | 128/644 |
| 3,279,468 | 10/1966 | LeVine | 128/792 |
| 3,498,291 | 3/1970 | Bunn | 128/644 |
| 3,508,541 | 4/1970 | Westbrook et al. | 128/644 |
| 4,317,457 | 3/1982 | Guillot | 128/763 |

FOREIGN PATENT DOCUMENTS

| | | | |
|---|---|---|---|
| 2481924 | 11/1981 | France | 128/82.1 |
| 1437121 | 5/1976 | United Kingdom | 128/640 |

Primary Examiner—Lee S. Cohen
Attorney, Agent, or Firm—Kinney & Lange

[57] ABSTRACT

A transcutaneous electrode device permits an electrical signal to be transmitted to or received from an anatomical site of a human patient when that site is covered by an intervening plaster or synthetic cast. The device includes a flange assembly and a collar assembly (which cooperate to capture the cast and define an aperture through the cast) and an electrode tampon assembly (which is inserted through the aperture to provide electrical contact to the anatomical site). The electrode tampon assembly includes an external barrel or carrier which is insertable in the aperture, an electrically conductive medium (such as a sponge saturated with a conductive fluid) carried at the distal end of the barrel, and an electrical connector at the proximal end of the barrel. A coil spring urges the conductive medium into contact with the anatomical site and provides electrical connection between the conductive medium and the electrical connector.

31 Claims, 4 Drawing Figures

U.S. Patent  Aug. 20, 1985  4,535,779
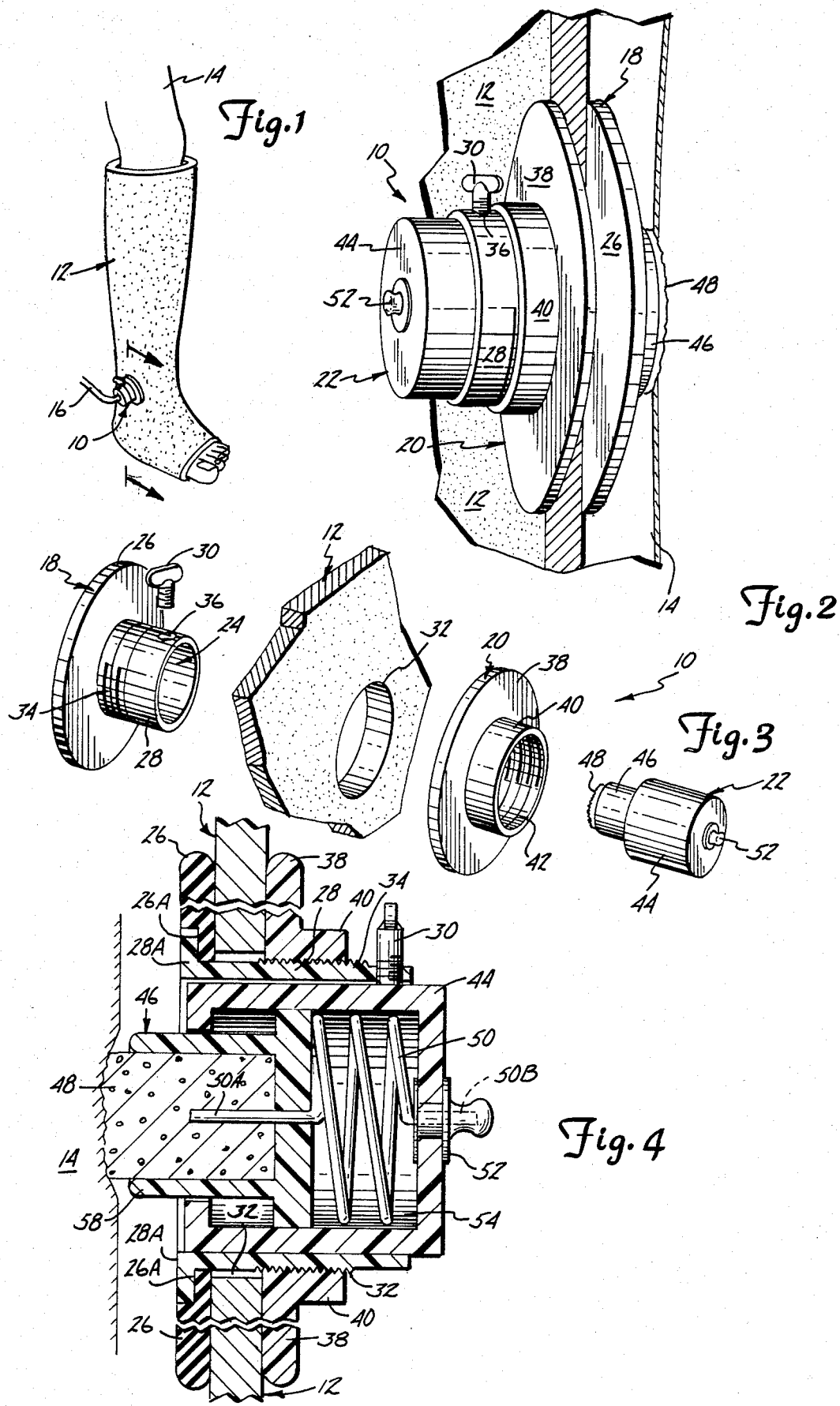

TRANSCUTANEOUS ELECTRODE DEVICE FOR CAST-COVERED SITES

BACKGROUND OF THE INVENTION

1. Field of the Invention

The present invention relates to device for transmitting electrical signals to or receiving electrical signals from a human patient. In particular, the present invention relates to a transcutaneous electrode device for electrical connection to an anatomical site which is covered by a cast.

2. Description of the Prior Art

Medical electrodes which are attached to the skin of a patient have been used for many years. With the ever-increasing sophistication of medical electronics, medical electrodes are continually finding new and wider uses. One type of medical electrode may be termed a "monitoring" electrode, which is used in conjunction with monitoring equipment such as electrocardiograph and electroencephalograph equipment.

Another common type of medical electrode may be termed a "transmitting" or "stimulating" electrode. This type of electrode is used with a transcutaneous electrical stimulator to apply electrical current to the patient's body for treatment of pain, muscle stimulation, or the regeneration of tissue.

There are instances when it would be advantageous to apply either a monitoring or a transmitting electrode to a patient's skin, but that site is covered by an intervening plaster or synthetic cast, because the patient has one or more fractured bones. For example, the application of transcutaneous electrical nerve stimulation can relieve pain associated with the fracture, or can prevent muscle atrophy in a portion of the body which is covered by the cast. In other cases, the application of electrical current to the patient's skin can be used to stimulate regneration of bone tissue at the fracture site.

In the prior art, the application of an electrode to a site covered by a cast has required "windowing" of the cast by cutting the hardened cast with a cast saw. A conventional monitoring or transmitting electrode is then placed in direct contact with the skin and is connected to a monitoring device or a stimulator. This procedure has significant disadvantages.

First, although cast saws have been developed that are generally quite safe, small abrasions or cuts of the patient's skin can still occur during the windowing procedure.

Second, the windowing can result in structural weakness of the cast.

Third, in some cases the particular area of the body does not allow for windowing at all. This can be due to the nature of the fracture or the location of the fracture. For example, the electrical current may be required to be applied directly to the fracture site, which is generally the least desirable place to cut a window in the cast.

Fourth, it is often difficult to apply and remove the electrodes through the window without bothering either the cast or the area of the body which is covered by the cast.

Fifth, in order to maintain contact with the skin, the electrode typically must have an adhesive layer. As a result, the electrode leaves a residue on the skin which is difficult to clean through the window.

There is a continuing need for an improved device and method for transmitting and receiving electrical signals from the skin at an anatomical site which is covered by an intervening cast. In particular, there is a need for a device which is simple in construction, simple to use, and maintains the structural integrity of the cast, while permitting reliable electrical contact to the patient's skin.

SUMMARY OF THE INVENTION

The present invention is an device which provides electrical connection to an anatomical site through an intervening cast which covers that site. The device includes support means attached to and supported by the cast for defining an aperture through the cast, and an electrode which is insertable in the aperture and which provides electrical contact to the anatomical site. The electrode includes a carrier which is removably insertable in the aperture, an electrically conductive medium carried at a distal end of the carrier for making electrical contact with the anatomical site when the carrier is inserted in the aperture, and electrical connection means adjacent the proximal end of the carrier for providing electrical connection to the conductive medium.

In preferred embodiments of the present invention, the device includes means for attaching the carrier to the support means in a fixed position and bias means for providing a resilient bias force which urges the conductive medium into contact with the anatomical site. This maintain contact between the conductive medium and the site without requiring an adhesive. In addition, it ensures conductive contact between the conductive medium and the patient's body despite any relative shifting of the cast and the body.

The support means is preferably a flange assembly and a collar assembly which are placed in position when the cast is being formed. The flange assembly is located on the inner surface of the cast (i.e. the surface closest to the patient's body), while the collar assembly is located on the outer surface of the cast. When the collar and flange assembly are connected together, the cast is trapped and held securely between them.

BRIEF DESCRIPTION OF THE DRAWINGS

FIG. 1 is a perspective view showing a leg cast containing the transcutaneous electrode device of the present invention.

FIG. 2 is a perspective view, partially in section, showing the transcutaneous electrode device of FIG. 1.

FIG. 3 is an exploded view of the transcutaneous electrode device.

FIG. 4 is a sectional view along section 4—4 of FIG. 1.

DETAILED DESCRIPTION OF THE PREFERRED EMBODIMENTS

Transcutaneous electrode device 10 of the present invention is a device which permits transmission of an electrical signal to an anatomical site or reception of an electrical signal from an anatomical site when that site is covered by an intervening cast 12. In FIG. 1, cast 12 is in the form of a leg cast which covers the lower portion of leg 14 of a human patient. In the particular embodiment shown in FIG. 1, transcutaneous electrode device 10 is connected by electrical wire 16 to a transcutaneous electrical stimulator (not shown). Electrical current is supplied through wire 16 to transcutaneous electrode device 10, and thereby to the patient's skin which underlies transcutaneous electrode device 10. The electrical current is applied to achieve a desired physiological response, such as regeneration of bone growth at a fracture site, or the transcutaneous electrical stimulation of nerves for the treatment of pain or the prevention of muscle atrophy.

Although the embodiment shown in FIG. 1 involves a cast 12 covering a portion of leg 14, the present invention is applicable to casts which cover other portions of a patient's body. Similarly, although transcutaneous electrode device 10 shown in FIG. 1 is for the purpose of transmitting electrical signals to an anatomical site covered by cast 12, the present invention is equally applicable to the reception of electrical signals from sites on the patient's body which are covered by cast 12. In that case, transcutaneous electrode device 10 is connected by wire 16 to electrical monitoring equipment, such as an electocardiograph or an electroencephalograph.

FIGS. 2-4 show a preferred embodiment of transcutaneous electrode device 10 in further detail. In this embodiment, transcutaneous electrode device 10 includes three major components, flange assembly 18, collar assembly 20, electrode tampon assembly 22. Flange assembly 18 and collar assembly 20 together form a support which is attached to and supported by cast 12, and which defines an aperture 24 through cast 12. Electrode tampon assembly 22 is inserted through aperture 24 to make physical and electrical contact to the skin of leg 14 which underlies aperture 24.

In the preferred embodiment shown in FIGS. 2-4, flange assembly 18 consists of plate 26, sleeve 28, and thumbscrew 30. Plate 26 is preferably made of a relatively soft and flexible rubber or synthetic material, while sleeve 28 is preferably a relatively hard material, such as a plastic. Sleeve 28 is fitted through plate 26 and has a flange portion 28A which mates with a circular groove 26A in plate 26 (as shown in FIG. 4). Sleeve 28 projects through opening 32 in cast 12 to define aperture 24 into which electrode tampon assembly 22 is inserted. A portion of sleeve 28 contains external threads 34. Sleeve 28 also includes a threaded hole 36 into which thumbscrew 30 is inserted to hold electrode tampon assembly 22 in place.

Collar assembly 20 is preferably an integral plate 38 and sleeve 40 having internal threads 42 which mate with external threads 34 of sleeve 28. When collar assembly 20 is threaded onto flange assembly 18, cast 12 is held between plate 26 of flange assembly 18 and plate 38 of collar assembly 20. In a preferred embodiment of the present invention, collar assembly 20 is formed of a relatively hard material (preferably the same material as sleeve 28).

Electrode tampon assembly 22 includes external barrel 44, internal barrel or plunger 46, conductive medium 48, bias spring 50, and snap connector 52. External barrel 44, in the preferred embodiment shown in FIGS. 2-4, is a cylindrical barrel having an outer diameter which is slightly less than the inner diameter of opening 24 defined by flange assembly 18. External barrel 44 is preferably formed of a relatively hard and rigid electrically insulating plastic material. Barrel 44 has a hollow core or chamber 54 and an opening at its distal end. Internal plunger 46 is mounted for sliding movement within chamber 54. Plunger 46 includes a flange section located within chamber 54, and a cylindrical cup section 58 which projects out of chamber 54 through the opening. Internal plunger 46 is preferably a relatively soft electrically insulating plastic material, so that the outer ends of cup section 58 do not abrade the skin of leg 14.

Cup section 58 carries conductive medium 48, which is in a preferred embodiment a sponge saturated with a conductive material such as a conductive fluid or gel. The outer end of conductive medium 48 contacts the skin of leg 14, to make electrical contact with leg 14.

When electrode assembly 22 is mounted in opening 24 and is fixed in place by set screw 30, conductive means 48 is urged into contact with the skin of leg 14 by compression spring 50. Spring 50 provides a bias force which urges plunger 46 toward leg 14, and thus maintains conductive medium 48 in intimate contact with the skin of leg 14.

In the preferred embodiment shown in FIG. 4, compression spring 50 also performs a second function: it provides electrical connection between conductive medium 48 and snap connector 52. As shown in FIG. 4, end 50A of spring 50 projects through the flange section of plunger 46 and is embedded in conductive medium 48. Opposite end 50B of spring 50 projects into and is captured by snap connector 52. In this embodiment, spring 50 is a metal and thus an electrical conductor, and a current path is established between conductive medium 48 and snap connector 52 through spring 50.

The installation of transcutaneous electrode device 10 is preferably performed during the application of cast 12 to leg 14. This process is generally as follows:

The physician casts the affected limb or body area (in this case leg 14) up to the selected anatomical site. Thumbscrew 30 is removed from sleeve 28, and sleeve 28 is then fitted through plate 26 to form flange assembly 18. While holding flange assembly 18 against the desired anatomical site, the physician wraps the cast over plate 26. Before the cast has completely dried or set up, collar assembly 20 is fitted over sleeve 28 and is screwed down until cast 12 is trapped securely between plate 26 of flange assembly 18 and plate 38 of collar assembly 20. Cast 12 is then allowed to dry, with flange assembly 18 and collar assembly 20 securely in place.

Electrode tampon assembly 22 is inserted through opening 24 in sleeve 28 until internal barrel plunger 46 and conductive medium 48 make contact with the skin surface at the electrode site. Some compression of spring 50 is desirable, in order to ensure that a bias force is applied against plunger 46 to maintain contact between conductive medium 48 and the skin even if slight shifts in relative position of leg 14 and cast 12 cause the gap between leg cast 12 and leg 14 to increase. Thumbscrew 30 is then inserted into threaded hole 36 and tightened down until external barrel 44 of electrode tampon assembly 22 is held firmly in place. Lead wire 16 with a female snap connector (not shown) is attached to snap connector 52 to provide a connection between transcutaneous electrode device 10 and the stimulating or monitoring equipment.

The transcutaneous electrode device 10 of the present invention has a number of important advantages over the prior art procedures and devices used to transmit signals to an anatomical site or to receive signals from that site when the site is covered by a cast.

First, in the prior art the cast typically must be "windowed" by the physician in order to then apply a conventional monitoring or stimulating electrode. As discussed previously, windowing a cast can result in cuts and abrasions to the patient. With the present invention, this windowing procedure is not required.

Second, the present invention does not degrade the structural integrity of the cast. In fact, the installation of flange assembly 18 and collar assembly 20 while cast 12 is being formed can actually enhance the strength of cast 12.

Third, electrode tampon assembly 22 is soft and resilient so that it does not abrade the skin surface, even if there are slight shifts in position of cast 12 or leg 14.

Fourth, the bias force provided by spring 50 and the flexibility and compressibility of conductive medium 48 allow intimate contact with the skin surface without the need for an adhesive. As a result, electrode tampon assembly 22 is easily removable without leaving any residue on the skin.

Fifth, with the present invention the skin surface at the anatomical site can be easily checked by the physician or patient to determine if there has been any skin reaction or breakdown.

Sixth, electrode tampon assembly 22 is easily inserted and removed, and therefore the patient can change transcutaneous electrode device 10 as often as necessary.

Seventh, conductive medium 48 also acts as a storage chamber which holds the conductive fluid required to make good contact to the skin surface over a extended period of time.

Eighth, the simple construction of electrode tampon assembly 22 and the use of relatively inexpensive materials allows electrode tampon assembly 22 to be a disposable assembly. This is much more convenient, particularly for the patient.

Ninth, because flange assembly 18 and collar asembly 20 engage both the inner and outer surfaces of cast 12, electrode tampon assembly 22 is held securely in position. Electrode tampon assembly 22 is not pressed out of cast 12 if an external force is applied to cast 12. In addition, the resilience and compressibility of electrode tampon assembly 22 (due to conductive medium 48 and spring 50) accommodate such an external force without injuring the patient.

Tenth, after cast 12 has been removed from leg 14, flange assembly 18 and collar assembly 20 are removable from cast 12 and can be reused repeatedly. This is particularly advantageous because casts are often changed several tims during a recuperative phase. When one cast is removed, the physician merely unscrews flange assembly 18 and collar assembly 20, and they are ready for use again with a new cast.

FIGS. 2–4 illustrate the one of the highly advantageous embodiments of the transcutaneous electrode device of the present invention. The various assemblies which form transcutaneous electrode device 10, however, can also take other forms. For example, in some embodiments of the present invention, plunger 46 and compression spring 50 of electrode tampon assembly 22 are replaced by a tube of a honeycomb configuration which acts as a storage chamber for a conductive medium. In that case, the honeycomb structure of the tube provides a bias force which urges the exposed end of the conductive medium into contact with the skin surface, and therefore a separate compression spring is not required.

In other embodiments of the present invention, the components which are attached to cast 12 and which define opening 24 through cast 12 differ from the specific flange assembly 18 and collar assembly 20 illustrated in FIGS. 2–4. For example, in some embodiments of the present invention, the connection of flange assembly 18 and collar assembly 20 is by means of a twist or snap lock arrangement, rather than external threads 34 and internal threads 42 as shown in FIGS. 3 and 4.

In still other embodiments of the present invention, the support apparatus which is attached to cast 12 is attached to cast 12 after rather than during formation of cast 12. In those embodiments, the support apparatus preferably includes an assembly which is inserted through an opening in a cast, and then expands to a size larger than the opening through the cast, so that the support apparatus engages both the inner and outer surfaces of the cast. In still other embodiments, a support apparatus is attached to the other side of the cast by screws or other fasteners, and provides the opening into which electrode tampon assembly 22 is inserted.

Although the present invention has been described with reference to preferred embodiments, workers skilled in the art will recognize that changes may be made in form and detail without departing from the spirit and scope of the invention.

What is claimed is:

1. An apparatus for providing electrical connection to anatomical site through an intervening cast which surrounds a portion of a patient's body and overlies and restricts access to the site, the apparatus comprising:

support means adapted to be attached to and supported by the cast in spaced relationship to the site for defining an aperture through the cast; the support means comprising:

aperture defining means for extending through the cast to define the aperture through the cast which is aligned with the site;

first and second cast engaging means extending generally radially outward from the aperture defining means for engaging interior and exterior surfaces of the cast, respectively; and connection means for connecting the first and second cast engaging means and the aperture defining means in fixed relationship;

an electrode comprising:

a carrier which is insertable into the aperture from outside the cast toward the anatomical site and removable from the aperture by movement away from the anatomical site;

an electrically conductive medium carried at a first end of the carrier for making electrical contact to the anatomical site when the carrier is inserted in the aperture; and electrical connection means adjacent a second end of the carrier for providing electrical connection to the electrically conductive medium; and means for releasably holding the carrier in a fixed position with respect to the support means when the carrier is inserted in the aperture.

2. The apparatus of claim 1 and further comprising:

bias means for providing a resilient bias force which urges the conductive medium into contact with the anatomical site.

3. The apparatus of claim 2 wherein the bias means is carried by the carrier.

4. The apparatus of claim 1 wherein the carrier has a chamber, and wherein the conductive medium is positioned in the chamber and extends out of the chamber at the first end of the carrier.

5. The apparatus of claim 3 wherein the electrode further comprises:

bias means positioned in the chamber for providing a resilient bias force which urges the conductive medium toward the anatomical site.

6. The apparatus of claim 4 wherein the bias means comprises a compression spring.

7. The apparatus of claim 6 wherein the compression spring is an electrical conductor and wherein a first end of the compression spring is in contact with the conductive medium and a second end of the compression spring is in contact with the electrical connection means to provide an electrically conductive path between the conductive medium and the electrical connection means.

8. The apparatus of claim 4 wherein the electrode further comprises:
a plunger movable in the chamber carrying the conductive medium, wherein the bias means applies the bias force to the plunger.

9. The apparatus of claim 7 wherein the plunger has a cup portion which holds the conductive medium.

10. The apparatus of claim 9 wherein the conductive medium comprises a compressible, resilient absorbent body saturated with an electrically conductive material.

11. The apparatus of claim 1 wherein the aperture defining means comprises a first sleeve which is attached to the first cast engaging means and which is adapted to project through an opening in the cast.

12. The apparatus of claim 11 wherein the connection means comprises:
first and second connector means carried by the first sleeve and the second cast engaging means, respectively, for mating engagement to connect the first and second cast engaging means with the cast held therebetween.

13. The apparatus of claim 12 wherein the second cast engaging means comprises a cast engaging plate and a second sleeve, the second sleeve being coaxially aligned with and surrounding the first sleeve.

14. The apparatus of claim 13 wherein the first connector means comprises screw threads on an outer surface of the first sleeve, and wherein the second connector means comprises screw threads on an inner surface of the second sleeve.

15. The apparatus of claim 1 wherein the first and second cast engaging means comprise first and second plates, respectively, which are connected together by the connection means in generally parallel relationship so that the cast is held therebetween.

16. The apparatus of claim 15 wherein the first plate is a flexible member.

17. The apparatus of claim 1 wherein the conductive medium is a compressible, resilient, nonadhesive material.

18. The apparatus of claim 17 wherein the conductive medium comprises a synthetic sponge material filled with a conductive material.

19. An apparatus for providing a connection between an anatomical site covered by a cast and a medical device, the cast being of a type which surrounds a portion of a patient's body and overlies and restricts access to the site, the apparatus comprising:
first cast engaging means for engaging an interior surface of the cast;
second cast engaging means for engaging an exterior surface of the cast;
connection means for connecting the first and second cast engaging means so that the cast is held therebetween;

aperture defining means for extending through the cast and supported by one of the first and second cast engaging means to define an aperture through the cast which is aligned with the site;
site engaging means which is insertable into the aperture from outside the cast for engaging the site to connect the site with the medical device and which is removable from the aperture by movement away from the site; and
means for releasably holding the site engaging means in a fixed position with respect to the first and second cast engaging means when the site engaging means is positioned in the aperture.

20. The apparatus of claim 18 wherein the aperture defining means comprises a first sleeve which is attached to the first cast engaging means and which is adapted to project through an opening in the cast.

21. The apparatus of claim 20 wherein the connection means comprises:
first and second connector means carried by the first sleeve and the second cast engaging means, respectively, for mating engagement to connect the first and second cast engaging means with the cast held therebetween.

22. The apparatus of claim 21 wherein the second cast engaging means comprises a cast engaging plate and a second sleeve, the second sleeve being coaxially aligned with and surrounding the first sleeve.

23. The apparatus of claim 22 wherein the first connector means comprises screw threads on an outer surface of the first sleeve, and wherein the second connector means comprises screw threads on an inner surface of the second sleeve.

24. The apparatus of claim 19 wherein the first and second cast engaging means comprise first and second plates, respectively, which are connected together by the connection means in generally parallel relationship so that the cast is held therebetween.

25. The apparatus of claim 24 wherein the first plate is a flexible member.

26. The apparatus of claim 19 wherein the means insertable into the aperture comprises a compressible, resilient, nonadhesive electrically conductive medium for electrically contacting the anatomical site.

27. The apparatus of claim 26 and further comprising:
bias means for providing a bias force which urges the conductive medium into contact with the anatomical site.

28. Medical apparatus for treatment of an anatomical site on a patient's body, the apparatus comprising:
a cast which, when in use, surrounds a portion of the patient's body, the cast having an interior surface closer to the patient's body and an exterior surface further from the patient's body, the cast overlying and restricting access to an anatomical site on the patient's body;
a sleeve extending through and surrounding by the cast, the sleeve defining an aperture through the cast which is aligned with the anatomical site;
first and second cast engaging means extending generally radially outward from the sleeve for engaging the interior and exterior surfaces, respectively, of the cast, one of the first and second cast engaging means being connected to the sleeve;
connection means for connecting the first and second cast engaging means so that the cast is held therebetween;

an electrode insertable into the aperture from outside the cast and adapted for making electrical contact with the anatomical site, the electrode being removable from the aperture by movement away from the anatomical site; and means for releasably holding the electrode in a fixed position with respect to the sleeve when the electrode is in engagement with the anatomical site.

29. A method of providing electrical connection to an anatomical site of a patient when a portion of the patient's body which includes the site is to be covered with a cast, the method comprising:

positioning a flange assembly over the site, the flange assembly including a first sleeve having an aperture therethrough and a first plate which surrounds the first sleeve;

applying cast material over the portion of the patient's body so that the first plate is covered by the cast material and the first sleeve projects through the cast material;

connecting a collar assaembly to the first sleeve so that a portion of the cast material surrounding the first sleeve is held between the first plate and the collar assembly; and inserting an electrode assembly into the aperture so that the electrode assembly is supported by the flange assembly and the collar assembly and is in electrical contact with the site.

30. The method of claim 29 wherein the collar assembly comprises a second sleeve which surrounds a portion of the first sleeve and a second plate which surrounds the second sleeve, and wherein the cast material surrounding the first sleeve is held between the first plate and the second plate.

31. The method of claim 29 wherein the step of connecting the collar assembly to the first sleeve is performed before the cast material is fully hardened.

* * * * *